United States Patent [19]
Jun et al.

[11] Patent Number: 6,075,170
[45] Date of Patent: Jun. 13, 2000

[54] PROCESS FOR PREPARING CYCLOHEXANOL AND CYCLOHEXANONE

[75] Inventors: Ki Won Jun, Daejeon; Sang Bum Kim, Seoul; Seong Bo Kim; Kyu Wan Lee, both of Daejeon, all of Rep. of Korea

[73] Assignee: Korea Research Institute of Chemical Technology, Rep. of Korea

[21] Appl. No.: 09/029,661

[22] PCT Filed: Dec. 14, 1995

[86] PCT No.: PCT/KR95/00162

§ 371 Date: Sep. 1, 1998

§ 102(e) Date: Sep. 1, 1998

[87] PCT Pub. No.: WO97/08119

PCT Pub. Date: Mar. 6, 1997

[30] Foreign Application Priority Data

Aug. 28, 1995 [KR] Rep. of Korea ............ 95/26858

[51] Int. Cl.⁷ ............... C07C 35/08; B01J 23/44
[52] U.S. Cl. ............................ 568/836; 502/326
[58] Field of Search ............... 568/836; 502/326

[56] References Cited

U.S. PATENT DOCUMENTS 5,208,392  5/1993  Lee et al. ................... 568/836

FOREIGN PATENT DOCUMENTS 0 087 924  9/1983  European Pat. Off. .
0 469 662  2/1992  European Pat. Off. .
60-92236   5/1985  Japan .

OTHER PUBLICATIONS

Jun et al. Hydroxylation of cyclohexane with hydrogen and oxygen in acetone and silica–supported iron–palladium catalysts. Chem.–ing.–Tech. 64 (7), pp. 637–639. Abstract only. (1992) No. month found.

*Primary Examiner*—Ralph Gitomer
*Assistant Examiner*—Majorie A. Moran
*Attorney, Agent, or Firm*—Finnegan, Henderson, Farabow, Garrett & Dunner, LLP

[57] ABSTRACT

This invention relates to a process for preparing cyclohexanol and cyclohexanone, in particular, to a process for preparing cyclohexanol and cyclohexanone by selectively oxidizing cyclohexane with Fe/Pd catalyst in a flow of hydrogen and oxygen gases in the mixture of acetone and acetic acid.

10 Claims, No Drawings

PROCESS FOR PREPARING CYCLOHEXANOL AND CYCLOHEXANONE

This application is an international application PCT/KR95/00162, with an international filing date of Dec. 14, 1995, which entered the national stage in the U.S. under 35 U.S.C. § 371 as application Ser. No. 09/029,661, and further claim the benefit of the Korean patent application No. 1995/26858, filed Aug. 28, 1995.

BACKGROUND OF THE INVENTION

1. Field of the Invention

This invention relates to a process for preparing cyclohexanol and cyclohexanone, in particular, to a process for preparing cyclohexanol and cyclohexanone by selectively oxidizing cyclohexane with Fe/Pd catalyst in a flow of hydrogen and oxygen gases in the mixture of acetone and acetic acid.

Cyclohexanol and cyclohexanone are available as intermediates for synthesizing nylon-6 and nylon-6,6 and generally produced by oxidation of cyclohexane on an industrial scale. But the conventional processes of preparing cyclohexanol and cyclohexanone have some deficiencies that these processes require a condition of high temperature over 150° C. and high pressure over 8 atm and its conversion is as low as 4%. Further, the product selectivity cannot exceed 80% because various decomposed oxidation-products of cyclohexane are produced from these reactions.

Because of the above problems, continuous researches on more effective and selective processes for preparing cyclohexanol and cyclohexanone have been conducted. For example, European patent appln. No. 83-87,924 discloses a process for preparing alcohol or ketones by oxidizing parraffinic hydrocarbons in a reaction system which employs iron catalyst, hydrogen sulfide, acetic acid, pyridine solvent and oxygen. But the resulting mixture shows poor separation and recovery of catalyst and products and especially, a large amount of pyridine is used compared to the amount of reaction product. Therefore, the problems of economical deficience and toxicity were raised.

As another example, in Japanese patent unexamined publication 85-92,236, cyclohexanone was acquired by adding oxygen to cyclohexene but there remains a problem that the manufacture of cyclohexene is more difficult that that of cyclohexane.

Additionally, the inventors of this invention discloses in U.S. Pat. No. 5,208,392 a method for preparing cyclohexanol and cyclohexanone with about 3~7% yields with no byproducts, by the oxidation of cyclohexane in hydrogen and oxygen gases with Fe/Pd catalyst in acetone solvent.

This invention is an improvement of U.S. Pat. No. 5,208,392 in that the activity and the stability of catalyst are improved through ligand binding with iron catalyst by using the solvent mixture of acetone and acetic acid instead of pure acetone solvent. As the result, yields of cyclohexanol and cyclohexanone increased significantly compared with those of U.S. Pat. No. 5,208,392. And especially, the more reaction time is extended and the more yields increase greatly up to about 4~12% because the deactiviation of catalyst is reduced. Moreover, there is little or nothing of byproducts during the oxidation of cyclohexane and the recovering and reusing of solid Fe/Pd catalyst is very easy.

SUMMARY OF THE INVENTION

The object of this invention is to provide a new process for preparing cyclohexanol and cyclohexanone with high yields.

This invention is characterized in using the mixture of acetone (1 weight parts) and acetic acid (0.05~1.5 weight parts) in preparing cyclohexanol and cyclohexanone by oxidation of cyclohexane with Fe/Pd catalyst.

DETAILED DESCRIPTION OF THIS INVENTION

This invention is based on the catalytic abilities, that is, that of palladium catalyst is to convert molecular hydrogen and oxygen added to the solvent into hydrogen peroxide; and that of iron catalyst is to use the said hydrogen peroxide in the oxidation of hydrocarbons and it is characterized in using the mixture of acetone and acetic acid as a solvent. The said acetic acid acts as a ligand for iron catalyst and plays a role to improve the activity and the stability of iron catalyst.

In this invention, iron and palladium are used as catalysts and they can be used respectively or properly mixed together as solid catalysts.

The iron catalyst of this invention employs iron salt such as $Fe^{2+}$ or $Fe^{3+}$, or iron oxide such as $FeCl_2$, $FeCl_3$, $FeO$, $Fe_2O_3$, $FeSO_4$, $Fe_2(SO_4)_3$ or $Fe(OAc)_2$ with no special pretreatment. And the palladium catalyst of this invention employs palladium metal or palladium salts (for example, $PdCl_2$, $Pd(NO_3)_2$ etc.) supported by an appropriate carrier which is selected from alumina, silica, silica-alumina and carbon.

The ratio of iron and palladium used as catalysts in this reaction is preferable to be 0.02~1 weight parts of palladium to 1 weight parts of iron. It is not desirable to use a large amount of palladium catalyst because the rate of decomposing the produced hydrogen peroxide by the palladium catalyst becomes larger than that of using the produced hydrogen peroxide by the iron catalyst.

The solid Fe/Pd catalyst can be prepared by impregnating a solution of palladium compound onto iron oxide (for example, $FeO$, $Fe_3O_4$, $Fe_2O_3$ etc.). Explained more in detail, after preparing the solution of a palladium compound such as palladium chloride or palladium nitrate, it is impregnated onto an iron oxide, dried at 100~150° C. for 2~24 hours and calcined at 300~600° C. for 2~15 hours in a flow of air or hydrogen. Thus the solid state catalyst is prepared. The prepared solid catalyst is pretreated to increase its activity before used in the preparation of cyclohexanol and cyclohexanone. The pretreatment is to contact 1 weight parts of solid catalyst with the mixed gases of hydrogen and oxygen for 10~50 hours in the solution of 1~20 weight parts of cyclohexane and 4~50 weight parts of acetone-acetic acid mixture and dry it at 80~150° C. for 10~30 hours. The acetone and acetic acid used in the pretreatment is prepared by mixing 1 weight parts of acetone with 0.05~1.5 weight parts of acetic acid and hydrogen and oxygen gases are respectively provided at a rate of 0.2~10 by volume per minute.

In this invention, another important thing is to use a proper reaction medium such as acetone and acetic acid mixture. If acetone is not used in reaction medium, all the reacting compounds such as hydrogen peroxide, hydrogen, oxygen and cyclohexane cannot be dissolved evenly and the reaction cannot be proceeded efficiently. And if acetic acid is not mixed, high yields and efficient reuse of the catalyst, which are characteristics of this invention, cannot be expected. The ratio of acetone and acetic acid is preferable within the range from 1:0.05 to 1:1.5 by weight. If the acetic acid is used in large amount, the solvent effect for evenly dissolving the reactants becomes low.

In this invention, the cyclohexanol and cyclohexanone is prepared by adding the above-mentioned Fe/Pd catalyst to the solution of acetone-acetic acid and flowing hydrogen and oxygen gases to it. And at this time, it is desirable to use cyclohexane in an amount of 1~20 times of the Fe/Pd catalyst by weight and the mixture of acetone and acetic acid in an amount of 4~50 times of the Fe/Pd catalyst by weight is desirable. If cyclohexane is used less than 1 times of the total amount of the Fe/Pd catalyst by weight, the reaction system becomes inefficient because the amount of products, which can be produced for the reaction, is too small compared with the amount of catalyst. And if it is more than 20 times by weight, the reaction slows down because the amount of catalyst becomes too small compared with the amount of the reactants. If the used amount of acetone and acetic acid mixture is less than 4 times by weight, the yield increase by the reaction-medium effect is not given because the amount of reaction medium becomes too small compared with the whole amount of reaction system and if it exceeds 50 times in weight, reaction rate cannot be expected to be efficiently high because the concentration of catalyst and reactants become too low. And the hydrogen and oxygen gases may be respectively provided at a rate of 0.2~10 by volume per minute to solution and dissolved. But at this time, if the each amount of flowed hydrogen and oxygen is less than 0.2 by volume per minute, the yields are decreased due to low concentration thereof and if it exceeds 10 by volume per minute, the reaction system becomes inefficient because the gas flow is too high to be dissolved. The reaction is carried out under a mild condition, e.g. at an atmospheric pressure and at a temperature between 10~50° C. and the reactant and the solvent evaporated during the reaction is reused by refluxing in a refrigerated condenser.

As explained in the above, the process of preparing cyclohexanol and cyclohexanone in this invention by oxidizing cyclohexane with hydrogen and oxygen gases is characterized in that Fe/Pd catalyst is used as a catalyst and the mixture of acetone and acetic acid is used as a solvent. And compared with the conventional processes, the yield in this invention is greatly increased and especially in long time reaction, the increase is noticable because the deactivation of catalyst can be prevented.

This invention is illustrated by the following Examples, which should not be taken to limit the scope of the invention. And the yields are calculated by the following equations;

$$\text{Yield of cyclohexanol (\% by moles)} = \frac{\text{moles of produced cyclohexanol}}{\text{moles of provided cyclohexane}} \times 100$$

$$\text{Yield of cyclohexanone (\% by moles)} = \frac{\text{moles of produced cyclohexanone}}{\text{moles of provided cyclohexane}} \times 100$$

EXAMPLE 1

After adding $FeCl_2 \cdot 4H_2O$ (0.3 g), Pd/alumina(Pd content 1%, 1 g) and cyclohexane (5 g) to the mixture of acetone (17 ml) and acetic acid (3 ml), it was stirred in a flow of hydrogen and oxygen gases at the respective rate of 20 ml/min. As the result of reaction for 3 hours at 30° C. under atmospheric pressure, 3.94 mole % of cyclohexanol and 0.83 mole % cyclohexanone with the total yield of 4.77 mole % were obtained.

EXAMPLE 2

After adding $FeCl_2 \cdot 4H_2O$ (1 g), Pd/alumina(Pd content 1%, 3 g) and cyclohexane (5 g) to the mixture of acetone (17 ml) and acetic acid (3 ml), it was stirred in a flow of hydrogen and oxygen gases at the respective rate of 20 ml/min. As the result of reaction for 3 hours at 30° C. under atmospheric pressure, 6.83 mole % of cyclohexanol and 1.24 mole % cyclohexanone with the total yield of 8.07 mole % were obtained.

EXAMPLE 3

After adding $FeCl_2 \cdot 4H_2O$ (0.5 g), Pd/alumina(Pd content 1%, 1 g) and cyclohexane (5 g) to the mixture of acetone (17 ml) and acetic acid (3 ml), it was stirred in a flow of hydrogen and oxygen gases at the respective rate of 20 ml/min. As the result of reaction for 17 hours at 30° C. under atmospheric pressure, 8.84 mole % of cyclohexanol and 2.13 mole % cyclohexanone with the total yield of 10.97 mole % were obtained.

EXAMPLE 4

The reaction is carried out in the same manner as in Example 3 except that the reaction time was 24 hours, and in result, 8.21 mole % of cyclohexanol and 3.32 mole % cyclohexanone with the total yield of 11.53 mole % were obtained.

EXAMPLE 5

After adding $FeCl_2 \cdot 4H_2O$ (0.1 g), Pd/alumina(Pd content 2%, 1 g) and cyclohexane (5 g) to the mixture of acetone (20 ml) and acetic acid (1 ml), it was stirred in a flow of hydrogen and oxygen gases at the respective rate of 20 ml/min. As the result of reaction for 3 hours at 30° C. under atmospheric pressure, 4.03 mole % of cyclohexanol and 0.65 mole % cyclohexanone with the total yield of 4.68 mole % were obtained.

EXAMPLE 6

After adding $FeCl_2 \cdot 4H_2O$ (0.3 g), Pd/alumina(Pd content 1%, 1 g) and cyclohexane (5 g) to the mixture of acetone (19 ml) and acetic acid (1 ml), it was stirred in a flow of hydrogen and oxygen gases at the respective rate of 20 ml/min. As the result of reaction for 3 hours at 30° C. under atmospheric pressure, 3.50 mole % of cyclohexanol and 0.62 mole % cyclohexanone with the total yield of 4.12 mole % were obtained.

EXAMPLE 7

After adding $FeCl_2 \cdot 4H_2O$ (0.3 g), Pd/alumina(Pd content 1%, 1 g) and cyclohexane (5 g) to the mixture of acetone (15 ml) and acetic acid (5 ml), it was stirred in a flow of hydrogen and oxygen gases at the respective rate of 20 ml/min. As the result of reaction for 3 hours at 35° C. under atmospheric pressure, 4.01 mole % of cyclohexanol and 0.74 mole % cyclohexanone with the total yield of 4.75 mole % were obtained.

EXAMPLE 8

After adding $FeCl_2 \cdot 4H_2O$ (0.3 g), Pd/alumina(Pd content 1%, 1 g) and cyclohexane (5 g) to the mixture of acetone (10 ml) and acetic acid (10 ml), it was stirred in a flow of hydrogen and oxygen gases at the respective rate of 20 ml/min. As the result of reaction for 3 hours at 36° C. under atmospheric pressure, 3.40 mole % of cyclohexanol and 0.69 mole % cyclohexanone with the total yield of 4.09 mole % were obtained.

EXAMPLE 9

After adding $FeCl_3 \cdot 6H_2O$ (0.4 g), Pd/alumina(Pd content 1%, 1 g) and cyclohexane (5 g) to the mixture of acetone (17 ml) and acetic acid (3 ml), it was stirred in a flow of hydrogen and oxygen gases at the respective rate of 20 ml/min. As the result of reaction for 3 hours at 30° C. under atmospheric pressure, 4.22 mole % of cyclohexanol and 0.80 mole % cyclohexanone with the total yield of 5.02 mole % were obtained.

EXAMPLE 10

After adding $Fe_2O_3$ (1 g), Pd/silica (Pd content 1.3%, 1 g) and cyclohexane (5 g) to the mixture of acetone (20 ml) and acetic acid (1 ml), it was stirred in a flow of hydrogen and oxygen gases at the respective rate of 20 ml/min. As the result of reaction for 3 hours at 30° C. under atmospheric pressure, 3.13 mole % of cyclohexanol and 0.41 mole % cyclohexanone with the total yield of 3.54 mole % were obtained.

EXAMPLE 11

In 1.6 g of $PdCl_2$ in water(160 ml), $Fe_2O_3$ (8 g) was added and impregnated by evaporation. When the evaporation of water was completed, it was dried at 150° C. for 1.5 hours and calcined in a flow of the mixed gas of hydrogen and nitrogen(5% $H_2$+95% $N_2$) at 500° C. for 4 hours and at 500° C. for 8 hours in a flow of air. As the result of reaction, $Pd/Fe_2O_3$ catalyst was prepared.

After adding cyclohexane (5 g), acetone 17 ml) and acetic acid (3 ml) to $Pd/Fe_2O_3$ (1 g), it was stirred in a flow of hydrogen and oxygen gases at the respective rate of 20 ml/min. As the result of reaction for 16 hours at 30° C. under atmospheric pressure, 3.63 mole % of cyclohexanol and 2.45 mole % cyclohexanone with the total yield of 6.08 mole % were produced.

EXAMPLE 12

After adding cyclohexane (5 g), acetone (17 ml) and acetic acid (3 ml) to $Pd/Fe_2O_3$ (1 g), which was prepared by the same manner in Example 11, it was stirred at 30° C. for 48 hours in a flow of hydrogen and oxygen gases at the respective rate of 20 ml/min., filtered and dried for 24 hours in oven of 120° C. in order to activate the catalyst. To the activated catalyst (1 g), cyclohexane (5 g), acetone(17 ml) and acetic acid (3 ml) were added and stirred in a flow of hydrogen and oxygen gases at the respective rate of 20 ml/min. As the result of reaction for 16 hours at 30° C. under atmospheric pressure, 4.25 mole % of cyclohexanol and 7.25 mole % cyclohexanone with the total yield of 11.50 mole % were obtained.

COMPARATIVE EXAMPLE 1

1.3 mole % of cyclohexanol and 0.27 mole % cyclohexanone with total yield of 1.57 mole % were obtained by the same manner in Example 1 except that pure acetone (20 ml) was used as solvent instead of the acetone and acetic acid mixture.

COMPARATIVE EXAMPLE 2

0.58 mole % of cyclohexanol and 0.20 mole % cyclohexanone with the total yield of 0.78 mole % were obtained by the same manner in Example 1 except that pure acetone (20 ml) was used as solvent instead of the acetone and acetic acid mixture.

COMPARATIVE EXAMPLE 3

The catalyst was activated by the same manner with Example 12 except that pure acetone (20 ml) was used as solvent instead of the acetone and acetic acid mixture. 1.76 mole % of cyclohexanol and 0.77 mole % cyclohexanone with the total yield of 2.53 mole % were obtained by the same manner in Example 5 except that pure acetone (20 ml) was used as solvent instead of the acetone and acetic acid mixture.

What is claimed is:

1. A process for preparing cyclohexanol and cyclohexanone by oxidizing cyclohexane with an Fe/Pd catalyst in a flow of hydrogen and oxygen gases, and in the presence of a mixture of acetone and acetic acid wherein the ratio of acetone to acetic acid ranges from 1:0.05 to 1:1.5 by weight.

2. The process of claim 1, wherein the mixture of acetone and acetic acid is in an amount of 4 to 50 times by weight of the Fe/Pd catalyst.

3. The process of claim 1, wherein cyclohexane is in an amount of 1 to 20 times by weight of the Fe/Pd catalyst.

4. The process of claim 1, wherein the Fe/Pd catalyst is a mixture of a palladium compound supported by a carrier and an iron based compound.

5. The process of claim 4, wherein the iron based compound is selected from the group consisting of $FeCl_2$, $FeCl_3$, FeO, $Fe_2O_3$, $FeSO_4$, $Fe_2(SO_4)_3$, and $Fe(OAc)_2$.

6. The process of claim 4, wherein the carrier is selected from the group consisting of alumina, silica, silica-alumina, and carbon.

7. The process of claim 1, wherein the Fe/Pd catalyst is prepared by impregnating a palladium compound onto an iron oxide, followed by drying the impregnated iron oxide, and then calcining the dried oxide under air or hydrogen.

8. The process of claim 7, wherein the iron oxide is FeO, $Fe_3O_4$, or $Fe_2O_3$.

9. The process of claim 7, wherein the palladium compound is $PdCl_2$ or $[Pd(NO_3)_2]$.

10. The process of claim 7, wherein the catalyst is activated.

* * * * *